United States Patent [19]

McDowall et al.

[11] Patent Number: 5,498,463
[45] Date of Patent: Mar. 12, 1996

[54] POLYETHYLENE MELTBLOWN FABRIC WITH BARRIER PROPERTIES

[75] Inventors: Debra J. McDowall; Lawrence H. Sawyer, both of Roswell; David C. Strack, Canton; Terry K. Timmons, Marietta, all of Ga.

[73] Assignee: Kimberly-Clark Corporation, Neenah, Wis.

[21] Appl. No.: 215,220

[22] Filed: Mar. 21, 1994

[51] Int. Cl.$^6$ ............................ B32B 5/18; B32B 5/26; B32B 31/20; D04H 3/14; D04H 3/16

[52] U.S. Cl. .................. 428/198; 128/849; 156/62.4; 156/62.6; 156/62.8; 156/73.1; 156/308.4; 428/285; 428/286; 428/288; 428/311.5; 428/311.7; 428/315.9; 428/316.6; 428/903

[58] Field of Search .................. 156/62.4, 62.6, 156/62.8, 73.1, 308.4; 128/849; 428/198, 285, 286, 288, 296, 903, 311.5, 311.7, 315.9, 316.6

[56] References Cited

U.S. PATENT DOCUMENTS

| | | | |
|---|---|---|---|
| 3,338,992 | 8/1967 | Kinney | 264/24 |
| 3,341,394 | 9/1967 | Kinney | 161/72 |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,855,046 | 12/1974 | Hansen et al. | 161/150 |
| 3,909,009 | 9/1975 | Cvetko et al. | 274/37 |
| 3,978,185 | 8/1976 | Buntin et al. | 264/93 |
| 4,041,203 | 8/1977 | Brock et al. | 248/157 |
| 4,196,245 | 4/1980 | Kitson et al. | 428/198 |
| 4,275,105 | 6/1981 | Boyd et al. | 428/198 |
| 4,298,649 | 11/1981 | Meitner | 428/198 |
| 4,340,563 | 7/1982 | Appel et al. | 264/518 |
| 4,436,780 | 3/1984 | Hotchkiss et al. | 428/198 |
| 4,508,113 | 4/1985 | Malaney | 128/132 D |
| 4,555,811 | 12/1985 | Shimalla et al. | 2/51 |
| 4,586,606 | 5/1986 | Howey | 206/313 |
| 4,595,629 | 6/1986 | Mays | 428/286 |
| 4,766,029 | 8/1988 | Brock et al. | 428/286 |
| 4,818,597 | 4/1989 | DaPonte et al. | 428/284 |
| 4,830,907 | 5/1989 | Sawyer et al. | 428/225 |
| 4,863,785 | 9/1989 | Berman et al. | 428/218 |
| 4,880,691 | 11/1989 | Sawyer et al. | 428/225 |
| 4,891,957 | 1/1990 | Strack et al. | 66/192 |
| 4,909,975 | 3/1990 | Sawyer et al. | 264/210.7 |
| 5,073,436 | 12/1991 | Antonacci et al. | 428/219 |
| 5,149,576 | 9/1992 | Potts et al. | 428/198 |
| 5,169,706 | 12/1992 | Collier, IV et al. | 428/152 |
| 5,178,931 | 6/1992 | Perkins et al. | 428/198 |
| 5,208,098 | 5/1993 | Stover | 428/284 |

*Primary Examiner*—James C. Cannon
*Attorney, Agent, or Firm*—James B. Robinson

[57] ABSTRACT

A nonwoven fabric is provided which has good barrier properties, softness and breathability. A linear low density polyethylene is used in a meltblown layer in this invention to provide barrier properties comparable to polypropylene. The meltblown layer may be used in a multilayer laminate and the other layers may be comprised of bicomponent fibers. The fabric may be used in, for example, diapers, feminine hygiene products, adult incontinence products, wound dressings, bandages, sterilization wraps, surgical gowns and drapes and wipers.

17 Claims, 2 Drawing Sheets

POLYETHYLENE MELTBLOWN FABRIC WITH BARRIER PROPERTIES

BACKGROUND OF THE INVENTION

This invention relates generally to a nonwoven fabric or web which is formed from meltblown fibers of thermoplastic polyethylene resin, as well as the process of producing such a fabric.

Thermoplastic resins have been extruded to form fibers and webs for a number of years. The most common thermoplastics for this application are polyolefins, particularly polypropylene. Other materials such as polyesters, polyetheresters, polyamides and polyurethanes are also used for this purpose. Each material has its characteristic advantages and disadvantages visa vis the properties desired in the final product to be made from such fibers.

Nonwoven fabrics are useful for a wide variety of applications such as diapers, feminine hygiene products, incontinence products, towels, medical garments and many others. The nonwoven fabrics used in these applications are often in the form of laminates like spunbond/meltblown/spunbond (SMS) laminates. In SMS laminates the exterior layers are generally spunbond polypropylene which are usually present for strength, and the interior layer which is generally meltblown polypropylene and is usually present as a barrier layer.

It is desirable that the meltblown barrier fabric layer have good barrier properties yet also be as soft and drapeable as possible. Polypropylene meltblown fabrics, while usually possessing good barrier properties, are not as soft and drapeable as polyethylene fabrics. Polyethylene meltblown fabrics are generally very soft and drapeable yet usually lack the requisite barrier properties. The lack of sufficient barrier properties in polyethylene meltblown fabrics is thought to be due to the inability to form uniformly fine fibers or due to the tendency to generate "shot", an imperfection which causes gaps or holes in the webs.

It is an object of this invention to provide a meltblown fabric which has barrier properties comparable to polypropylene meltblown fabric yet with the softness and drapeability common to polyethylene fabrics.

SUMMARY OF THE INVENTION

A nonwoven fabric is provided which has barrier properties comparable to polypropylene meltblown fabrics yet has a softer hand than polypropylene and good breathability. This fabric is provided through a process of producing a soft nonwoven barrier fabric comprising the steps of melting at least one thermoplastic polyethylene polymer which has a density in the range of about 0.86 to about 0.97 grams/cc, extruding the polymer through fine openings, drawing said polymer to produce fibers, and depositing the fiberized polymer on a collecting surface to form a web of disbursed fibers, wherein the web has a hydrohead of at least 40 centimeters, and a cup crush peak load value of less than 40 grams. Such a web usually has a Frazier Porosity of less than 300 ft$^3$/ft$^2$/min.

The fabric may be laminated with spunbond layers of which one may be pre-bonded and may also be composed of bicomponent fibers.

The nonwoven fabric of this invention may be used in products such as, for example, diapers, training pants, feminine hygiene products, adult incontinence products, wound dressings, bandages, sterilization wraps, surgical drapes and gowns and wipers. One specific area in which the nonwoven fabric of this invention is useful is as a leakage barrier in personal care items as an outer cover, leg cuffs and containment flaps.

DETAILED DESCRIPTION OF THE INVENTION

DEFINITIONS

Figure 1:
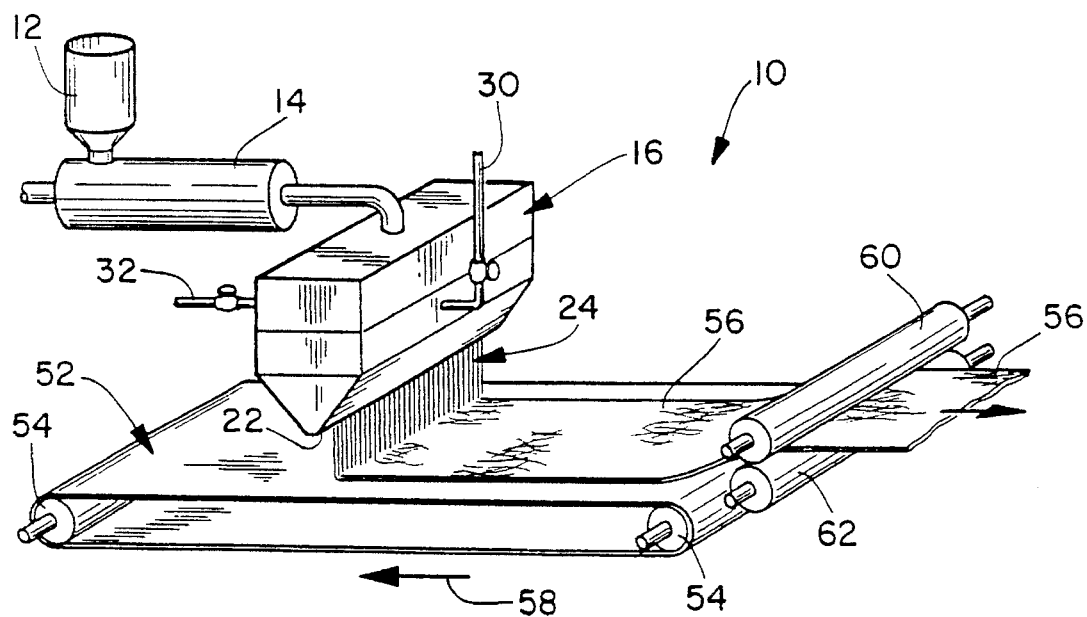
FIG. 1 is a schematic illustration of an apparatus which may be utilized to form the nonwoven web of the present invention.

As used herein the term "polymer" generally includes but is not limited to, homopolymers, copolymers (such as for example, block, graft, random and alternating copolymers), terpolymers, etc. and blends and modifications thereof. Furthermore, unless otherwise specifically limited, the term "polymer" shall include all possible geometrical configurations of the material. These configurations include, but are not limited to isotactic, syndiotactic and random symmetries.

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes.

As used herein the term "spunbonded fibers" refers to small diameter fibers which are formed by extruding molten thermoplastic polymer material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. Nos. 3,502,763 and 3,909,009 to Levy, and U.S. Pat. No. 3,542,615 to Dobo et al. Spunbond fibers are generally continuous and larger than 7 microns, more particularly, having an average diameter of greater than 10 microns.

As used herein the term "meltblown fibers" means fibers formed by extruding a molten thermoplastic polymer through a plurality of fine, usually circular, die capillaries as molten threads or filaments into a high velocity gas (e.g. air) stream which attenuates the filaments of molten thermoplastic polymer material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin and U.S. Pat. 3,978,185.

As used herein the term "bicomponent" refers to fibers which have been formed from at least two polymers extruded from separate extruders but spun together to form one fiber. The configuration of such a bicomponent fiber may be a sheath/core arrangement wherein one polymer is surrounded by another or may be a side by side arrangement or an "islands-in-the-sea" arrangement. The ratio of the polymers used in a bicomponent fiber may be 75/25, 50/50, 25/75, etc.

As used herein, the term "bonding window" means the range of temperature of the calender rolls or other heating means used to bond the nonwoven fabric together, over which such bonding is successful. For polypropylene spunbond, this calender bonding window is typically from about 260° F. to about 310° F. (125° C. to 154° C.). Below about 260° F. the polypropylene is not hot enough to melt and bond and above about 310° F. the polypropylene will melt excessively and can stick to the calender rolls. Polyethylene has an even narrower bonding window.

As used herein, the term "stitchbonded" means, for example, the stitching of a material in accordance with U.S. Pat. No. 4,891,957 to Strack et al.

As used herein, the term "garment" means any type of apparel which may be worn. This includes industrial work wear and coveralls, undergarments, pants, shirts, jackets, gloves, socks, and the like.

As used herein, the term "medical product" means surgical gowns and drapes, face masks, head coverings, shoe coverings, wound dressings, bandages, sterilization wraps, wipers and the like.

As used herein, the term "personal care product" means diapers, training pants, absorbent underpants, adult incontinence products, and feminine hygeine products and the like.

As used herein, the term "outdoor fabric" means a fabric which is primarily, though not exclusively, used outdoors. The applications for which this fabric may be used include car covers, boat covers, airplane covers, camper/trailer fabric, furniture covers, awnings, canopies, tents, agricultural fabrics and outdoor apparel.

TEST METHODS

Cup Crush: The softness of a nonwoven fabric may be measured according to the "cup crush" test. The cup crush test evaluates fabric stiffness by measuring the peak load and peak energy required for a 4.5 cm diameter hemispherically shaped foot to crush a 23 cm by 23 cm piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. The foot and the cup are aligned to avoid contact between the cup walls and the foot which could affect the peak load. The peak load is measured while the foot is descending at a rate of about 0.25 inches per second (38 cm per minute). A lower cup crush value indicates a softer laminate. A suitable device for measuring cup crush is a model FTD-G-500 load cell (500 gram range) available from the Schaevitz Company, Pennsauken, N.J. Cup crush load is measured in grams. Cup Crush energy is measured in gm-mm.

Hydrohead: A measure of the liquid barrier properties of a fabric is the hydrohead test. The hydrohead test determines the height of water (in centimeters) which the fabric will support before a predetermined amount of liquid passes through. A fabric with a higher hydrohead reading indicates it has a greater barrier to liquid penetration than a fabric with a lower hydrohead. The hydrohead test is performed according to Federal Test Standard No. 191A, Method 5514.

Frazier Porosity: A measure of the breathability of a fabric is the Frazier Porosity which is performed according to Federal Test Standard No. 191A, Method 5450. Frazier Porosity measures the air flow rate through a fabric in cubic feet of air per square foot of fabric per minute or $ft^3/ft^2/min$. (Convert $ft^3/ft^2/min$. to liters per square meter per minute ($l/m^2/min$) by multiplying by 304.8).

Melt Flow Rate: The melt flow rate (MFR) is a measure of the viscosity of a polymer. The MFR is expressed as the weight of material which flows from a capillary of known dimensions under a specified load or shear rate for a measured period of time and is measured in grams/10 minutes at 190° C. according to, for example, ASTM test 1238, condition E.

The fibers from which the fabric of this invention is made are produced by the meltblowing process which is known in the art and is described in, for example, U.S. Pat. No. 3,849,241 to Butin and U.S. Pat. No. 3,978,185.

The meltblowing process generally uses an extruder to supply melted polymer to a die tip where the polymer is fiberized as it passes through fine openings, forming a curtain of filaments. The filaments are drawn pneumatically and deposited on a moving foraminous mat, belt or "forming wire" to form the nonwoven fabric. Nonwoven fabrics may be measured in ounces per square yard (osy) or grams per square meter (gsm). (Multiplying osy by 33.91 yields gsm.)

The fibers produced in the meltblowing process are generally in the range of from about 0.5 to about 10 microns in diameter, depending on process conditions and the desired end use for the fabrics to be produced from such fibers. For example, increasing the polymer molecular weight or decreasing the processing temperature results in larger diameter fibers. Changes in the quench fluid temperature and pneumatic draw pressure can also affect fiber diameter. Finer fibers are generally more desirable as they usually produce greater barrier properties in the fabric into which they are made.

The fabric of this invention may be used in a single layer embodiment or as a multilayer laminate incorporating the fabric of this invention. Such a laminate may be formed by a number of different techniques including but not limited to using adhesive, needle punching, ultrasonic bonding, print bonding, thermal calendering and any other method known in the art. Such a multilayer laminate may be an embodiment wherein some of the layers are spunbond and some meltblown such as a spunbond/meltblown (SM) laminate or a spunbond/meltblown/spunbond (SMS) laminate, as disclosed in U.S. Pat. No. 4,041,203 to Brock et al. and U.S. Pat. No. 5,169,706 to Collier, et al. or wherein some of the layers are made from staple fibers. The fibers used in the other layers may be polyethylene, polypropylene or bicomponent fibers.

An SMS laminate, for example, may be made by sequentially depositing onto a moving conveyor belt or forming wire first a spunbond fabric layer, then a meltblown fabric layer and last another spunbond layer and then bonding the laminate in a manner described above. Alternatively, the three fabric layers may be made individually, collected in rolls, and combined in a separate bonding step.

In thermal calendering, various patterns for calender rolls have been developed. One example is the Hansen Pennings pattern with between about 10 and 25% bond area with about 100 to 500 bonds/square inch as taught in U.S. Pat. No. 3,855,046 to Hansen and Pennings. Another common pattern is a diamond pattern with repeating and slightly offset diamonds. Bond pattern and coverage area can vary considerably depending on the use to which the fabric will be put.

When the fabric of this invention is used as an SMS laminate, it has been found to be advantageous to "pre-bond" one of the spunbond layers. Pre-bonding is a step of (thermally) bonding a layer by itself using a pattern of 8 to 50% bond area or more particularly a pattern of about 25% bond area with many small pins. Pre-bonding is advantageous with polyethylene webs because of the relatively high heat of fusion and low melting point of polyethylene. It is believed that in order to supply enough heat to a polyethylene web to bond it, the heat addition must be done sufficiently slowly to avoid excessively melting the web and causing it to stick to the calender rolls. Pre-bonding one of the spunbond layers helps to reduce the intensity of temperature the laminate must be subjected to in the bonding step.

Pre-bonding also provides the fabric with greater abrasion resistance though it can reduce the drapeability somewhat. Since it is an objective of this invention that the web provide good barrier properties yet be soft and drapeable, pre-bonding should be kept to a minimum. Pre-bonding is optional and if desired should be restricted to only one layer for this reason.

After pre-bonding, the spunbond layer may then be combined with unbonded meltblown and spunbond layers and bonded with a more open bond pattern like the one mentioned above, preferably with a pattern having relatively larger pins. The temperature of bonding will vary depending on the exact polymers involved, the degree and strength of bonding desired, and the final use of the fabric.

The fabric of this invention may also be laminated with films, staple fibers, paper, and other commonly used materials.

Areas in which the fabric of this invention may find utility are garments, personal care products and medical products. The particular components of the personal care products where this fabric may be used are as leakage barriers such as containment flaps, outer covers and leg cuffs. Wipers may be for industrial use or for home use as countertop or bathroom wipes. Sterilization of the fabric for use as a sterile wrap should, of course, take place at a temperature lower than the melting point of any of the polymers used in the fabric or by alternative means such as gamma or other radiation techniques.

Turning now to the figures, particularly FIG. 1, it can be seen that an apparatus for forming the nonwoven web of this invention is represented by the reference number 10.

In forming the nonwoven web of the present invention, pellets, beads or chips (not shown) of a suitable material are introduced into a hopper 12 of an extruder 14. The extruder 14 has an extrusion screw (not shown) which is driven by a conventional drive motor (not shown). As the material advances through the extruder 14, due to rotation of the extrusion screw by the drive motor, it is progressively heated to a molten state. Heating of the material may be accomplished in a plurality of discrete steps with its temperature being gradually elevated as it advances through discrete heating zones of the extruder 14 toward a meltblowing die 16. The die 16 may be another heating zone where the temperature of the thermoplastic resin is maintained at an elevated level for extrusion. The temperature which will be required to heat the material to a molten state will vary somewhat depending upon exactly which material is utilized and can be readily determined by those in the art.

Figure 2:
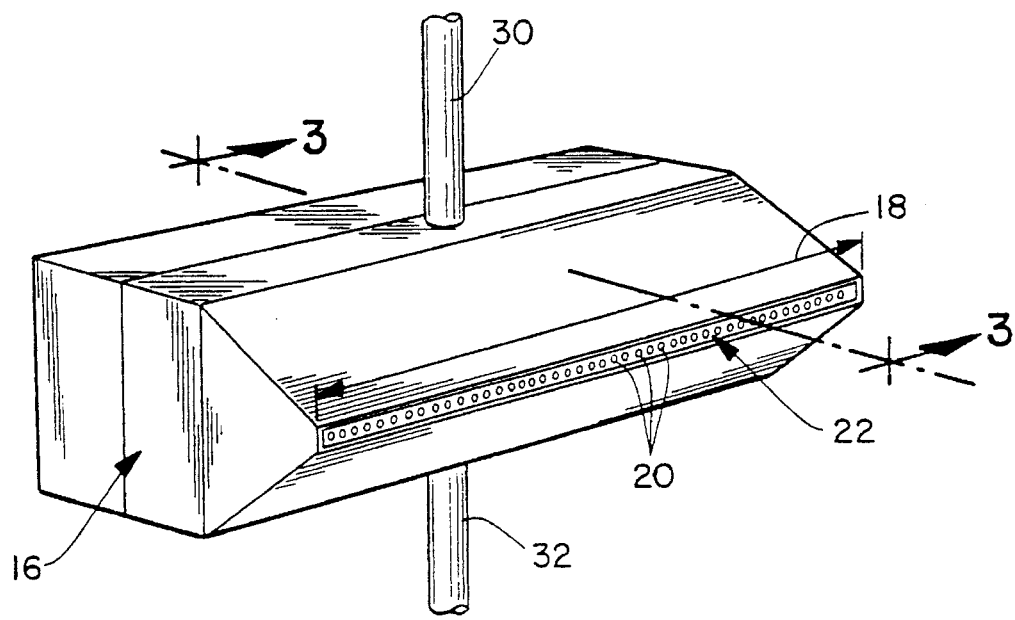
FIG. 2 is a bottom view of the die of FIG. 1 with the die having been rotated 90 degrees for clarity.

FIG. 2 illustrates that the lateral extent 18 of the die 16 is provided with a plurality of orifices 20 which are usually circular in cross-section and are linearly arranged along the extent 18 of the tip 22 of the die 16. The orifices 20 of the die 16 may have diameters that range from about 0.01 of an inch to about 0.02 of an inch and a length which may range from about 0.05 inches to about 0.30 inches. For example, the orifices may have a diameter of about 0.0145 inches and a length of about 0.113 inches. From about 5 to about 50 orifices may be provided per inch of the lateral extent 18 of the tip 22 of the die 16 with the die 16 extending from abut 20 inches to about 60 inches or more. FIG. 1 illustrates that the molten material emerges from the orifices 20 of the die 16 as molten strands or threads 24.

Figure 3:
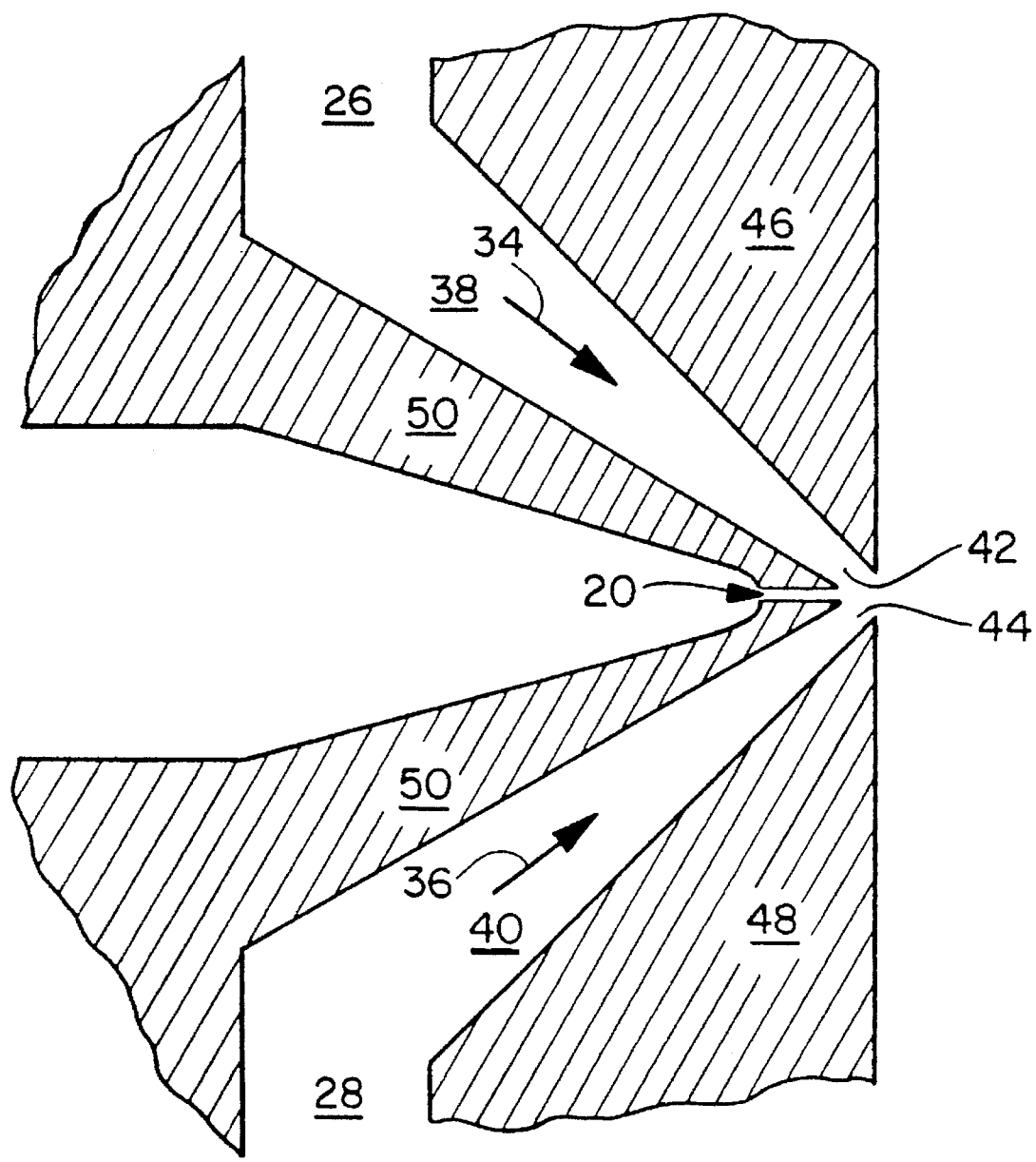
FIG. 3 is a cross-sectional view of the die of FIG 1 taken along line 3—3 of FIG. 2.

FIG. 3, which is a cross-sectional view of the die of FIG. 2 taken along line 3—3, illustrates that the die 16 preferably includes attenuating gas sources 30 and 32 (see FIGS. 1 & 2). The heated, pressurized attenuating gas enters the die 16 at the inlets 26, 28 and follows a path generally designated by arrows 34, 36 through the two chambers 38, 40 and on through the two narrow passageways or gaps 42, 44 so as to contact the extruded threads 24 as they exit the orifices 20 of the die 16. The chambers 38, 40 are designed so that the heated attenuating gas passes through the chambers 38, 40 and exits the gaps 42, 44 to form a stream (not shown) of attenuating gas which exits the die 16 on both sides of the threads 24. The temperature and pressure of the heated stream of attenuating gas can vary widely. For example, the heated attenuating gas can be applied at a temperature of from about 220° to about 315° C. (425°–600° F.), more particularly, from about 230° to about 280° C. The heated attenuating gas may generally be applied at a pressure of from about 0.5 pounds per square inch gage (psig) to about 20 psig. More particularly, from about 1 to about 10 psig.

The position of the air plates 46, 48 which, in conjunction with a die portion 50 define the chambers 38, 40 and the gaps 42, 44, may be adjusted relative to the die portion 50 to increase or decrease the width of the attenuating gas passageways 42, 44 so that the volume of attenuating gas passing through the air passageways 42, 44 during a given time period can be varied without varying the velocity of the attenuating gas. Furthermore, the air plates 46, 48 may be adjusted to effect a "recessed" die tip configuration as illustrated in FIG. 3, or a positive die tip 22 stick out configuration wherein the tip of the die portion 50 protrudes beyond the plane formed by the plates 48. Lower attenuating gas velocities and wider air passageway gaps are generally preferred if substantially continuous meltblown fibers or microfibers 24 are to be produced.

The two streams of attenuating gas converge to form a stream of gas which entrains and attenuates the molten threads 24, as they exit the orifices 20, into fibers or , depending on the degree of attenuation, microfibers of a small diameter which is usually less than the diameter of the orifices 20. The gas-borne fibers or microfibers 24 are blown, by the action of the attenuating gas, onto a collecting arrangement which, in the embodiment illustrated in FIG. 1, is a foraminous endless belt 52 conventionally driven by rollers 54. Other foraminous arrangements such as a rotating drum could be used. One or more vacuum boxes (not shown) may be located below the surface of the foraminous belt 52 and between the rollers 54. The fibers or microfibers 24 are collected as a coherent matrix of fibers on the surface of the endless belt 52 which is rotating as indicated by the arrow 58 in FIG. 1. The vacuum boxes assist in retention of the matrix on the surface of the belt 52. Typically, the tip 22 of the die 16 is from about 6 inches to about 14 inches from the surface of the foraminous belt 52 upon which the fibers are collected. The thus collected, entangled fibers or microfibers 24 are coherent and may be removed from the belt 52 as a self-supporting nonwoven web 56.

A number of process modifications were found to be helpful in order to produce the fabric of this invention. For example, the forming wire used in the practice of this invention should be of a finer mesh than that used for polypropylene meltblown fabric. In addition, the distance from the die tip to the forming wire or the "forming distance" should be reduced to about 7 inches (18 cm).

Polymers useful in the meltblowing process generally have a process melt temperature of between about 406° F. to about 608° F. (208° C. to 320° C.). Meltblown fibers for the practice of this invention are produced from particular polyethylene resins under particular operating conditions.

A particularly well suited polyethylene which may be used in this invention is available from the Dow Chemical Company of Freeport, Tex. under the trade name Aspun®. Aspun® designates a family of linear low density polyethylene resins. Acceptable resins are disclosed in U.S. Pat. 4,830,907 and are comprised of copolymers of ethylene with at least one alpha-olefin of $C_3$ to $C_{12}$ and have a density in the range of about 0.86 to 0.97 grams/cc and a melt flow rate in the range of about 0.01 to about 400 grams/10 minutes.

Any layer of a fabric of this invention may contain a fluorocarbon chemical to enhance chemical repellency which may be any of those taught in U.S. Pat. No. 5,178,931, column 7, line 40 to column 8, line 60. A particularly well suited additive is FX-1801, formerly called L-10307, which is available from the 3M Company of St. Paul, Minn. This material is identified as Additive M in the above cited patent and as having a melting point of about 130° to 138° C. This material may be added to a layer or layers at an amount of about 0.1 to about 2.0 weight percent or more particularly between about 0.25 and 1.0 weight percent. As noted in the above patent, the fluorocarbon additive is an internal additive, as differentiated from a topically applied additive, and preferentially migrates to the surface of the fibers as they are formed.

The layers of the fabric of this invention may also contain fire retardants for increased resistance to fire and/or pigments to give each layer the same or distinct colors. Fire retardants and pigments for spunbond and meltblown thermoplastic polymers are known in the art and are internal additives. A pigment, if used, is generally present in an amount less than 5 weight percent of the layer.

The fabric of this invention may also have topical treatments applied to it for more specialized functions. Such topical treatments and their methods of application are known in the art and include, for example, alcohol repellancy treatments, anti-static treatments and the like, applied by spraying, dipping, etc. An example of such a topical treatment is the application of Zelec® antistat (available from E.I. dupont, Wilmington, Del.).

The following Examples show the characteristics of fabrics which satisfy the requirements of this invention versus those that do not. Note that Examples 1, 4 & 5 are examples of the fabric of this invention, the others are not. The meltblown webs of this invention exhibit the fiber fineness and lack of shot required to produce hydrohead values of greater than 40 cm, cup crush peak load values of less than 40 grams and where the web usually has a Frazier Porosity of less than 300 ft$^3$/ft$^2$/min. The SMS laminates using the meltblown web of this invention have a hydrohead of at least 50 centimeters and a cup crush peak load value of less than 125 grams.

EXAMPLE 1

Meltblown fibers were produced from Dow's Aspun® XUR- 1567-45766-30A linear low density polyethylene resin. The polymer melt temperature was about 500° F. (260° C.), as was the drawing air which flowed at about 420 SCFM. The throughput was about 2 pounds per die plate inch per hour (357 gm/cm/hour) to produce a fabric with a basis weight of about 0.5 osy (17 gsm). The distance from the die tip to the forming wire was about 6 inches (15 cm). The results are shown in Table 1.

EXAMPLE 2

Meltblown fibers were produced from Dow's 61800.31 polyethylene resin. The polymer temperature was about 500° F. (260° C.), and the drawing air which flowed at about 315 SCFM was at a temperature of about 540° F. The throughput was about 2 pounds per die plate inch per hour (357 gm/cm/hour) to produce a fabric with a basis weight of about 0.7 osy (24 gsm). The distance from the die tip to the forming wire was about 8.5 inches (22 cm). The results are shown in Table 1.

EXAMPLE 2A

Meltblown fibers were produced from Dow's 61800.31 polyethylene resin, the same polymer as in Example 2, at slightly different conditions. The polymer temperature was about 500° F. (260° C.), and the drawing air which flowed at about 300 SCFM was at a temperature of about 510° F. The throughput was about 2 pounds per die plate inch per hour (357 gm/cm/hour) to produce a fabric with a basis weight of about 0.5 osy. The results are shown in Table 1.

EXAMPLE 3

Meltblown fibers were produced from Himont PF015 polypropylene resin. The polymer temperature was about 520° F. (270° C.), and the drawing air which flowed at about 370 SCFM was at a temperature of about 525° F. The throughput was about 3 pounds per die plate inch per hour (536 gm/cm/hour) to produce a fabric with a basis weight of about 0.5 osy (17 gsm). The distance from the die tip to the forming wire was about 9 inches (23 cm).

The results are shown in Table 1.

EXAMPLE 4

An SMS laminated fabric was produced. The spunbond layers were sheath/core bicomponent fibers with polyethylene as the sheath and polypropylene as the core. The polyethylene used in the spunbond layer was Dow's Aspun® 6811A and the polypropylene was from the Exxon Chemical Company of Baytown, Texas, and designated 3445. The spunbond melt temperature was about 430° F. (221° C.) and the throughput was 0.5 grams/hole/minute (ghm) to produce of fiber of 2.1 denier.

One of the spunbond layers was pre-bonded with a Hansen-Pennings pattern with about 25% bond area at a temperature of about 270° F.

The meltblown layer was the material of Example 1 above.

The layers were laminated together using an expanded Hansen-Pennings pattern at 300° F. The basis weight of the SMS fabric was 1.6 osy (54 gsm).

The results are shown in Table 1.

EXAMPLE 5

An SMS laminated fabric was produced like that in Example 4 using the same polymers. The spunbond melt temperature was about 440° F. (227° C.) and the throughput was 0.4 grams/hole/minute (ghm) to produce of fiber of 1.1 denier.

One of the spunbond layers was pre-bonded with a Hansen-Pennings pattern with about 25% bond area at a temperature of about 255° F.

The layers were laminated together at a temperature of about 280° F. (138° C.) using an expanded Hansen-Penning pattern. The basis weight of the fabric was 1.6 osy (54 gsm).

The results are shown in Table 1.

EXAMPLE 6

An SMS laminated fabric was produced. The spunbond layers were polypropylene homofiber. The polypropylene was Exxon's 9355 at a melt temperature of 420° F. (216° C.) and a throughput of 0.7 ghm for a fiber of 2.5 denier. The meltblown layer was the material of Example 3 above.

The layers were laminated together at a temperature of about 270° F. (132° C.) using a wire weave pattern. The basis weight of the fabric was 1.6 osy (54 gsm).

The results are shown in Table 1.

TABLE 1

| Example | Hydrohead | Frazier | Cup Crush Peak Load | Cup Crush Energy |
|---|---|---|---|---|
| 1 | 47 | 127 | 22 | 450 |
| 2 | 37 | 160 | 22 | 390 |
| 2A | 25 | 230 | na | na |
| 3 | 48 | 105 | 59 | 1190 |
| 4 | 58 | 50 | 100 | 1850 |
| 5 | 65 | 45 | 95 | 1760 |
| 6 | 46 | 38 | 195 | 4170 |

The results surprisingly show that fabrics made from fibers spun from polymers useful in this invention can have barrier properties comparable to and even somewhat better than conventional polypropylene fibers while having a softer feel and good breathability.

This invention desirably combines the good barrier properties associated with polypropylene meltblown fabrics with the softness associated with polyethylene meltblown fabrics to produce a soft, high barrier, fabric.

We claim:

1. A process of producing a soft nonwoven barrier fabric comprising the steps of;
   melting at least one thermoplastic polyethylene polymer, said polymer having a density in the range of about 0.86 to about 0.97 grams/cc;
   extruding said polymer through fine openings;
   drawing said polymer to produce fibers, and;
   depositing said fiberized polymer on a collecting surface to form a layer of meltblown disbursed fibers as a web, wherein said web has a hydrohead of at least 40 centimeters, and a cup crush peak load value of less than 40 grams.

2. The nonwoven fabric produced according to the method of claim 1 wherein said web has a Frazier Porosity of less than 300 ft$^3$/ft$^2$/min.

3. The nonwoven fabric produced according to the method of claim 1 further comprising the steps of adding a second layer of material to said layer of meltblown fibers and bonding the layers together.

4. The nonwoven fabric of claim 3 wherein said second layer is selected from the group consisting of spunbond fiber webs and staple fiber webs.

5. The nonwoven fabric of claim 4 wherein said second layer is comprised of fibers selected from the group consisting of polyethylene fibers, polypropylene fibers and polyethylene/polypropylene bicomponent fibers.

6. A nonwoven fabric laminate comprising a first layer, a second layer produced in accordance with the method of claim 1, and a third layer, wherein said first and third layers are selected from the group consisting of spunbond fiber webs and staple fiber webs, and which has been bonded to form a laminate.

7. The nonwoven fabric of claim 6 wherein said first and third layers are comprised of fibers selected from the group consisting of polyethylene fibers, polypropylene fibers and polyethylene/polypropylene bicomponent fibers.

8. The nonwoven fabric laminate of claim 6 wherein said fabrics are bonded by thermal calender bonding.

9. The nonwoven fabric laminate of claim 6 wherein said fabrics are bonded by ultrasonic bonding.

10. The nonwoven fabric of claim 6 which is present in an item selected from the group consisting of garments, medical products, personal care products and outdoor fabrics.

11. The nonwoven fabric of claim 6 which is laminated to a material selected from the group consisting of films, glass fibers, staple fibers, and papers.

12. The nonwoven fabric laminate of claim 6 wherein one of said first and third layers has been pre-bonded.

13. The nonwoven fabric laminate of claim 6 wherein said first and third layer fibers are bicomponent fibers comprised of polyethylene and polypropylene in a sheath/core arrangement with the polyethylene as the sheath.

14. A process of producing a soft nonwoven barrier fabric comprising the steps of;
   providing a polyethylene/polypropylene bicomponent sheath/core spunbond fiber web with polyethylene as the sheath as a first layer;
   melting at least one thermoplastic polyethylene polymer, said polymer having a density in the range of about 0.86 to about 0.97 grams/cc;
   extruding said polymer through fine openings;
   drawing said polymer to produce fibers, and;
   depositing said fiberized polymer on said web to form a layer of meltblown disbursed fibers as a second layer.

15. The method of producing the soft nonwoven barrier fabric of claim 14 further comprising the step of adding as a third layer a polyethylene/polypropylene bicomponent sheath/core spunbond fiber web to said first and second layers, with polyethylene as the sheath, against said second layer, wherein said fabric has a hydrohead of at least 50 centimeters and a cup crush peak load value of less than 125 grams.

16. The laminate of claim 15 which is present in an item selected from the group consisting of garments, medical products, personal care products and outdoor fabrics.

17. The laminate of claim 15 wherein said item is a medical product and said medical product is a surgical gown.

* * * * *

UNITED STATES PATENT AND TRADEMARK OFFICE
CERTIFICATION OF CORRECTION

PATENT NO. : 5,498,463

DATED : March 12, 1996

INVENTOR(S): McDowall et al.

It is certified that the following errors appear in the above-identified patent and that said Letters Patent is hereby corrected as shown below:

Column 1, line 16, "visa vis" should read --vis a vis--;
Column 2, line 13, "Fig" should read --Fig.--;

Signed and Sealed this

Seventeenth Day of December, 1996

BRUCE LEHMAN

*Attest:*

*Attesting Officer*           Commissioner of Patents and Trademarks